United States Patent [19]

Klettner

[11] Patent Number: 5,031,617

[45] Date of Patent: Jul. 16, 1991

[54] METHOD OF ALTERING HUMAN BLOOD GLUCOSE LEVELS BY THE APPLICATION OF ELECTRIC CHARGE

[76] Inventor: Harold L. Klettner, 3345 Beach Rd., Port Huron, Mich. 48060

[21] Appl. No.: 322,679

[22] Filed: Mar. 13, 1989

[51] Int. Cl.⁵ .............................................. A61N 1/10
[52] U.S. Cl. ................................ 128/419 R; 128/795; 128/796
[58] Field of Search ............... 128/381, 382, 795, 796, 128/419 R; 600/13, 14, 15

[56] References Cited

U.S. PATENT DOCUMENTS

| 309,897 | 12/1884 | Thurston | 128/795 |
|---|---|---|---|
| 4,428,366 | 1/1984 | Findl et al. | 600/14 |

FOREIGN PATENT DOCUMENTS 3702264  7/1987  Fed. Rep. of Germany ...... 128/796

Primary Examiner—Francis Jaworski
Assistant Examiner—Scott M. Getzow
Attorney, Agent, or Firm—Harness, Dickey & Pierce

[57] ABSTRACT

Human blood glucose levels can be altered by the application of electric charge. The application of electric charge to the human body results in decreased in vivo blood glucose levels.

15 Claims, No Drawings

METHOD OF ALTERING HUMAN BLOOD GLUCOSE LEVELS BY THE APPLICATION OF ELECTRIC CHARGE

BACKGROUND AND SUMMARY OF THE INVENTION

The present invention relates generally to a method of altering human blood glucose levels and, more specifically, to a method of treatment of hyperglycemic conditions by the application of electric charge to the body.

Hyperglycemic conditions such as those present in the diabetic can have serious and irreparable consequences, for example, blindness, impotence, and other problems resulting from impaired circulation. Conventional methods used to treat hyperglycemic conditions have had varying degrees of success. These methods include administration of pharmaceuticals such as anti-rejection and hypoglycemic agents, insulin injections and pumps and, more recently, pancreatic tissue transplants. Control of blood glucose levels through the application of a uniform, monopolar pulsed electromagnetic field has also met with some success, at least in test animals. U.S. Pat. No. 3,658,051, issued Jan. 31, 1984 to Findl et al. herein incorporated by reference. This method, however, although lowering blood glucose levels, does not reduce them to normal levels.

The method of the present invention provides a simple, non-invasive technique for altering human blood glucose levels by the application of electric charge. The method of the invention can be used to decrease in vivo blood glucose levels to normal or medically-acceptable levels by the application of electric charge directly to the human body.

DETAILED DESCRIPTION OF THE PREFERRED EMBODIMENTS

The method of the present invention generally comprises the application of electric charge to alter the level of glucose in human blood. The method of the invention further comprises treatment of hyperglycemic conditions in humans by the application of electric charge directly to the body.

The application of electric charge has been found to alter human blood glucose levels both in vitro and in vivo. Application of electric charge to human blood samples in vitro, i.e. outside the body, results in an increase in the glucose levels of the samples. However, and most surprisingly, as seen in the data set forth below, the application of charge to the human body produces a decrease of in vivo blood glucose levels. Moreover, it appears that application of electric charge will not decrease in vivo glucose levels below normal or medically-acceptable levels, a problem which may occur with other methods of treatment such as the administration of insulin. By normal or medically-acceptable glucose levels is meant a fasting blood glucose level in the range of approximately 60–140 mg/dl or approximately 100–200 mg/dl two hours after eating. Thus, the method of the invention can be utilized as a non-invasive treatment for hyperglycemic conditions such as diabetes.

When the method of the invention is used to treat hyperglycemic conditions, the subject being treated is first insulated from the ground and then contacted with a source of electric charge. The type of charge to be applied in accordance with the principles of the invention is preferably electrostatic charge, the source of which may be provided by any electrostatic generator, such as a Wimshurst apparatus or a Van de Graaff generator. Preferably, the source of charge is a Van de Graaff generator wherein voltage can be directly or indirectly controlled, for example, by altering the radius of the generator dome, changing the speed of the generator belt by a reostat, varying the distance of the motor pulley to the voltage terminal pulley, or varying the width of belt and pulleys.

The voltage and duration of charge applied to the body can be varied to adjust to individual factors such as age, size and surface area, the amount of body hair, the condition of the skin, the medical condition of the subject and atmospheric and environmental conditions. For an average adult subject with adult-onset diabetes, and having no additional serious medical problems such as certain cardiac conditions, the preferred maximum voltage applied is approximately in the range of 250,000 to 1,000,000 V, and the preferred duration of application per session is one to fifteen minutes. Preferably, the charge should be sufficiently low not to produce undue sensation or discomfort in the subject. Although a decrease in blood glucose may be apparent after only one session, it should be appreciated that a series of electric charge treatments to first acclimatize the subject may be necessary before a significant decrease in blood glucose levels is encountered after electric charging.

The mechanism of action of the electric charge on human blood glucose levels is not fully understood, and thus it is not intended that the method of the present invention be limited to any particular mechanism of action. However, with respect to the effect on the body which results in in vivo decreased glucose levels, one possibility is pancreatic stimulation, which may in turn increase insulin production. Another possibility is better utilization of insulin or glucose by the cells of the body. In any event, it is believed that when electric charge is applied to the body, the charge is conducted to the cells through the fiber system of the body which includes collagenous, reticular and elastic fibers, microtubules and other fibers and filaments. Thus, although the charge may be applied to any part of the body, preferred contact points for application of the electric charge are the palms and soles. The palms and soles of the human body contain a concentration of eccrine or "sweat" glands, approximately three thousand per square inch, which can function as electrical emitters and receivers.

Other medically-accepted recommendations for the treatment of hyperglycemia or diabetes, such as weight control, diet and exercise may be followed in addition to treatment by the method of the invention. Moreover, the method of the invention may be used in conjunction with other forms of treatment for hyperglycemic conditions such as administration of pharmaceuticals and insulin.

SPECIFIC EXAMPLES

EXAMPLE 1

Subject 1 was a 55-year old female diabetic: height 5'3.5"; weight 138 lbs.; blood pressure 110/80. The subject did not follow a restricted diet or take any medication throughout the course of the treatment, nor did she follow any exercise program other than normal routine activity. The subject's weight remained constant throughout the course of treatment described in this example.

The subject's fasting and two-hour after eating blood glucose levels were measured daily for a two-week period prior to the initiation of electric treatment. Fasting blood glucose readings were taken prior to breakfast. Two-hour glucose levels were taken two hours after dinner at approximately 7:30 p.m. Blood was obtained from the subject's finger by a lancet. Blood glucose levels were measured by the Accu-chek® II blood glucose monitor (6 volts) commercially available from Boehringer Mannheim Diagnostics of Indianapolis, Ind. and verified by the hexokinase method. The average fasting and two-hour glucose levels over the two-week period, as indicated in Table 1 below, were 181 mg/dl and 281 mg/dl, respectively.

Subject 1 then began daily treatment by electric charge applied in succession to the soles and palms using the following method: the subject stood barefoot on an aluminum conducting sheet connected to the high voltage terminal of a Van de Graaff generator having the following dimensions: dome diameter 13.5 in.; distance between pulleys 25.5 in.; total height 33 in. The aluminum conductor and subject standing thereon were insulated from the ground by a plastic pad of 12 mm thickness (8 sheets of 1.5 mm gauge plastic). The palms of the subject were also placed on a similar insulating pad. The generator was then turned on and brought up to a voltage of 500,000 V. The subject was charged through the soles for approximately three minutes at 500,000 V. After charging, the Van de Graaff generator was turned off and the subject stepped off the aluminum sheet to the ground.

After charging through the soles was accomplished and the subject grounded, the subject stood on the insulating pad and placed her palms firmly on the dome of the generator. The generator was again turned on and brought up to a voltage of 500,000 V. The subject was charged through the palms for another three minute period at 500,000 V. The generator was then turned off and the subject stepped off the insulative pad onto the ground.

Subject 1 was thus treated approximately two times a day, once after breakfast and once after dinner before retiring. The subject was treated over a nine-month period, except for three one-day periods when aggressive treatment by charging as described above three times a day was initiated to determine whether a drop below medically-acceptable levels could be obtained. Fasting blood glucose levels were measured before breakfast and two-hour blood glucose levels measured two hours after dinner before the evening treatment as previously described.

The after-treatment blood glucose levels shown in Table 1 below represent the blood glucose levels of samples taken approximately weekly and averaged within the monthly period indicated. As shown in Table 1, both fasting and two-hour blood glucose levels continued to decrease over the nine-month period of treatment. The amount of reduction of blood glucose levels recorded was as much as 150 mg/dl over a three-hour period. However, even after aggressive treatment by three sessions of charging in one day, as shown by the results in Table 2 below, a drop below normal or medically-acceptable levels was not encountered.

TABLE 1

| SUBJECT 1 | BLOOD GLUCOSE LEVEL | |
|---|---|---|
| PERIOD OF TREATMENT | FASTING BLOOD GLUCOSE | TWO-HOUR BLOOD GLUCOSE |
| Before treatment | 181 mg/dl | 281 mg/dl |
| 2 months | 156 mg/dl | 262 mg/dl |
| 4 months | 143 mg/dl | 260 mg/dl |
| 6 months | 136 mg/dl | 242 mg/dl |
| 8 months | 110 mg/dl | 180 mg/dl |
| 9 months | 100 mg/dl | 180 mg/dl |

TABLE 2

| SUBJECT 1 TIME | BLOOD GLUCOSE PROFILE DURING AGGRESSIVE TREATMENT BLOOD GLUCOSE LEVEL | |
|---|---|---|
| 12:15 p.m. | 262 mg/dl | (two hours after eating) |
| 12:30 p.m. | Treatment | |
| 1:05 p.m. | 206 mg/dl | |
| 1:35 p.m. | 155 mg/dl | |
| 2:05 p.m. | 110 mg/dl | |
| 2:35 p.m. | 98 mg/dl | |
| 2:55 p.m. | Treatment | |
| 3:55 p.m. | 77 mg/dl | |
| 8:35 p.m. | Treatment | |
| 11:00 p.m. | 90 mg/dl | |

EXAMPLE 2

Subject 2 was a 50-year old female diabetic: height 5'4"; weight 204 lbs; blood pressure 120/80. The subject's diet was moderately restricted and the subject was engaged in an exercise program of approximately one-half hour daily swimming or walking several months prior to and during the period of treatment. During the course of treatment, the subject's weight remained constant.

The subject's fasting and two-hour blood glucose levels prior to initiating electric treatments were obtained and measured over a two-week period as described in Example 1, and averaged 190 mg/dl and 228 mg/dl, respectively, as shown in Table 3 below.

Subject 2 was then electrostatically treated as described in Example 1, except that the treatments were for about 3.5 minutes each for palms and soles and the treatments were given only three times a week. The three weekly treatments were grouped into a 24-hour period, i.e. 9:30 p.m., and 9:30 a.m. and 8:30 p.m. the following day. This treatment regime was followed for five weeks. Following the five-week treatment plan, treatment was stopped for 47 days. After the 47-day period of no treatment, a regime of three treatments per day immediately following meals was begun. This course of treatment continued for twelve days, after which time treatment was stopped for twelve days. The resulting blood glucose levels, averaged over the indicated period of treatment or no treatment, is shown in Table 3 below.

TABLE 3

| SUBJECT 2 | BLOOD GLUCOSE LEVEL | |
|---|---|---|
| PERIOD OF TREATMENT/ NO TREATMENT | FASTING BLOOD GLUCOSE | TWO-HOUR BLOOD GLUCOSE |
| Before treatment | 190 mg/dl | 228 mg/dl |
| Five weeks of treatments (3 × week) | 173 mg/dl | 195 mg/dl |
| 47 days - no treatments | 166 mg/dl | 187 mg/dl |
| 12 days of treatments (3 × day) | 150 mg/dl | 170 mg/dl |

TABLE 3-continued

| SUBJECT 2 | BLOOD GLUCOSE LEVEL | |
|---|---|---|
| PERIOD OF TREATMENT/ NO TREATMENT | FASTING BLOOD GLUCOSE | TWO-HOUR BLOOD GLUCOSE |
| 12 days - no treatments | 127 mg/dl | 146 mg/dl |

It can be seen from the results in Table 3 that a substantial decrease in both fasting and two-hour blood glucose levels took place over an approximate fifteen-week period.

EXAMPLE 3

Subject 3 was a 42-year old male diabetic: height 6'1"; weight 265 lbs; blood pressure 160/85. The subject was being treated for hyperglycemia with Diabeta, ® two 5 mg tablets before breakfast and one tablet after dinner. The subject's average fasting blood glucose level was 236 mg/dl for the two-week period prior to initiation of electric treatment.

The subject was then treated in accordance with the method set forth in Example 1, once for four minutes each for palms and soles. As shown in Table 4 below, the subject experienced a decrease in glucose levels of 96 mg/dl over a three-hour period.

TABLE 4

| SUBJECT 3 (DIABETIC) TIME | BLOOD GLUCOSE PROFILE OVER TIME BLOOD GLUCOSE LEVEL |
|---|---|
| Before treatment | 236 mg/dl |
| 1 hour after treatment | 195 mg/dl |
| 2 hours after treatment | 164 mg/dl |
| 3 hours after treatment | 140 mg/dl |

EXAMPLE 4

Subject 4 was a 57-year old non-diabetic male: height 6'4"; weight 230 lbs; blood pressure 130/80, having a fasting blood glucose level of 76 mg/dl and a two-hour blood glucose level of 130 mg/dl. Table 5 below shows the blood glucose profile over time of the non-diabetic subject treated as described in Example 1 for 3.5 minutes each through the subject's soles and palms.

TABLE 5

| SUBJECT 4 TIME | BLOOD GLUCOSE PROFILE OVER TIME BLOOD GLUCOSE LEVEL |
|---|---|
| Before treatment | 76 mg/dl |
| 6:00 p.m. | 150 mg/dl (0.5 hours after eating) |
| 6:15 p.m. | Treatment |
| 6:35 p.m. | 157 mg/dl |
| 7:15 p.m. | 130 mg/dl |
| 8:15 p.m. | 76 mg/dl |
| 9:15 p.m. | 57 mg/dl |
| 10:15 p.m. | 56 mg/dl |
| 9:00 a.m. | 78 mg/dl (fasting reading) |

EXAMPLE 5

A control blood sample was obtained from diabetic Subject 1 and non-diabetic Subject 4 during fasting and two-hours after eating and the blood glucose levels measured by the method of Example 1. After the blood glucose levels of the control sample was measured, additional blood was extruded from the finger of the subject, left on the finger and then electrostatically charged outside the body by contacting the soles of the subject with the high-voltage terminal of the Van de Graaff generator by the method of Example 1. In each case, the generator was brought up to approximately 500,000 V and the sample charged for about 3 minutes. The glucose levels of the treated samples were then measured by Accu-Chek ® II.

In contrast to the reduced in vivo glucose levels experienced within the body after electric charge, the detectable in vitro blood glucose of the samples treated outside the body increased, as shown in the Tables 6 and 7 below. The blood glucose levels indicated in Tables 6 and 7 are averages for thirteen samples taken from diabetic subject 1, and twelve samples from non-diabetic Subject 4 which were electrostatically treated as described above.

TABLE 6

| DIABETIC BLOOD SAMPLE TREATMENT | BLOOD GLUCOSE LEVEL | |
|---|---|---|
| | FASTING SAMPLE | NON-FASTING SAMPLE |
| Before Treatment | 100 mg/dl | 286 mg/dl |
| 3 minutes at 500,000 V | 120 mg/dl | 313 mg/dl |

TABLE 7

| NON-DIABETIC BLOOD SAMPLE TREATMENT | BLOOD GLUCOSE LEVEL | |
|---|---|---|
| | FASTING SAMPLE | NON-FASTING SAMPLE |
| Before Treatment | 76 mg/dl | 150 mg/dl |
| 3 minutes at 500,000 V | 94 mg/dl | 165 mg/dl |

EXAMPLE 6

The reduction of fasting and two-hour blood glucose levels in Subjects 1, 2, 3 and 4 before and after treatment in accordance with the method of present invention as described above were compared and are set forth in Table 8 below. The before treatment levels indicated in Table 8 are averages of blood glucose levels taken daily over a two-week period.

The two/four-hour before treatment blood glucose levels were measured two hours after eating. The after treatment fasting blood glucose levels were measured three hours after treatment with no intervening meals. The after treatment two/four-hour blood glucose levels were measured two hours after treatment which was administered two hours after eating. After treatment values for Subject 1 are averages of five readings over 17 days, for Subject 2 averages of five readings over five weeks, and for Subjects 3 and 4 one reading each.

TABLE 8

| SUBJECT/TREATMENT | | BLOOD GLUCOSE LEVEL | |
|---|---|---|---|
| SUBJECT | TREATMENT | FASTING BLOOD GLUCOSE | TWO/FOUR-HOUR BLOOD GLUCOSE |
| SUBJECT 1 | Before treatment | 181 mg/dl | 281 mg/dl |
| | After treatment | 98 mg/dl | 126 mg/dl |
| SUBJECT 2 | Before treatment | 190 mg/dl | 228 mg/dl |
| | After treatment | 118 mg/dl | 146 mg/dl |
| SUBJECT 3 | Before treatment | 238 mg/dl | 320 mg/dl |
| | After treatment | 140 mg/dl | 164 mg/dl |
| SUBJECT 4 | Before treatment | 76 mg/dl | 130 mg/dl |
| | After treatment | 57 mg/dl | 76 mg/dl |

As shown above in Table 8, all subjects experienced a decrease in blood glucose levels after treatment in accordance with the method of the present invention.

It will be appreciated that those skilled in the art, once given the benefit of the foregoing disclosure, may now make modifications of the specific embodiments described herein without departing from the spirit of the present invention. Such modifications are to be considered within the scope of the present invention, which is solely limited by the scope and spirit of the appended claims.

What is claimed is:

1. A method of altering the in vivo blood glucose level in human blood comprising the steps of:
   providing a source of electrostatic charge;
   insulating said blood from the ground; and
   treating said blood with said electrostatic charge for a duration of time sufficient to alter the glucose level of said blood to within medically-acceptable blood glucose levels.

2. The method of claim 1, wherein said blood glucose level is an in vivo blood glucose level in a human body and said step of treating said blood further comprises contacting the skin of said body with said electrostatic charge.

3. The method claim 2, wherein said body is in a hyperglycemic state.

4. The method of claim 2, wherein said electrostatic charge is applied to the palms of said body.

5. The method of claim 2, wherein said electrostatic charge is applied to soles of said body.

6. A method of altering the in vivo blood glucose level in human blood comprising the steps of:
   providing a source of electrostatic charge;
   insulating said blood from the ground; and
   treating said blood with said electrostatic charge for a duration of time sufficient to alter the glucose level of said blood, wherein said step of treating said blood further comprises contacting the skin of said body with said electrostatic charge, and wherein said electrostatic charge is in the range of approximately $2.5 \times 10^5$ to $1 \times 10^6$ volts and said duration of time is in the range of approximately one to fifteen minutes.

7. A method for treatment of hyperglycemia in a living human body comprising the steps of:
   providing a source of electrostatic charge external from said body;
   insulating said body from the ground; and
   applying said electrostatic charge to said body for a duration of time sufficient to decrease the level of blood glucose in the blood after said application to within medically-acceptable levels.

8. The method of claim 7, wherein the method further comprises the step of increasing the voltage of said external source of electrostatic charge to a predetermined level.

9. The method of claim 7, wherein the step of applying said charge to the body further comprises the step of applying said charge to the skin of said body.

10. The method of claim 9, wherein said step of applying said charge to the skin further comprises applying said charge to the skin of the palms and soles of the body.

11. A method for treatment of hyperglycemia in a living human body comprising the steps of:
   providing a source of electrostatic charge external from said body;
   insulating said body from the ground; and
   applying said electrostatic charge to said body for a duration of time sufficient to decrease the level of blood glucose in the blood after said application, wherein the method further comprises the step of increasing the voltage of said external source of electrostatic charge to a predetermined level, and wherein said level of voltage and said duration of time are sufficient to reduce glucose levels to within medically-acceptable ranges.

12. A method for treatment of hyperglycemia in a living human body comprising the steps of:
   providing a source of electrostatic charge external from said body;
   insulating said body from the ground; and
   applying said electrostatic charge to said body for a duration of time sufficient to decrease the level of blood glucose in the blood after said application, wherein said method further comprises the step of increasing the voltage of said external source of electrostatic charge to a predetermined level, and wherein said predetermined level of voltage is in the range of approximately $2.5 \times 10^5$ to $1 \times 10^6$ volts.

13. A method for treatment of hyperglycemia in a living human body comprising the steps of:
   providing a source of electrostatic charge external from said body;
   insulating said body from the ground; and
   applying said electrostatic charge to said body for a duration of time sufficient to decrease the level of blood glucose in the blood after said application, wherein the step of applying said charge to the body further comprises the step of applying said charge to the skin of the body, and wherein said duration of time is in the range of approximately one to fifteen minutes.

14. A method for treatment of hyperglycemia in a living human body comprising the steps of:
   providing a source of electrostatic charge external from said body;
   insulating said body from the ground; and
   applying said electrostatic charge to said body for a duration of time sufficient to decrease the level of blood glucose in the blood after said application, wherein said steps are repeated until said glucose levels reach medically-acceptable levels.

15. A method for controlling the blood glucose levels of a human body comprising the steps of:
   providing a source of electrostatic charge of a predetermined voltage;
   insulating said body from the ground; and
   applying said charge to said body for a duration of time, wherein said predetermined voltage and said duration of time are sufficient to maintain said blood glucose level within medically-acceptable ranges.

* * * * *

UNITED STATES PATENT AND TRADEMARK OFFICE
CERTIFICATE OF CORRECTION

PATENT NO.   :   5,031,617

DATED        :   July 16, 1991

INVENTOR(S)  :   Harold L. Klettner

It is certified that error appears in the above-identified patent and that said Letters Patent is hereby corrected as shown below:

Column 6, line 64, Table 8: "238 mg/dl" should be --236 mg/dl--

Column 7, line 27, after "method" insert --of--

Signed and Sealed this

Eighth Day of December, 1992

Attest:

DOUGLAS B. COMER

Attesting Officer        Acting Commissioner of Patents and Trademarks